United States Patent [19]

Walker

[11] 4,135,051

[45] Jan. 16, 1979

[54] PROCESS FOR PREPARING ARYLALKANOIC ACID DERIVATIVES

[75] Inventor: Jerry A. Walker, Kalamazoo Township, Kalamazoo County, Mich.

[73] Assignee: The Upjohn Company, Kalamazoo, Mich.

[21] Appl. No.: 807,032

[22] Filed: Jun. 16, 1977

[51] Int. Cl.$^2$ .................. C07C 67/00; C07C 69/76
[52] U.S. Cl. .................. 560/105; 260/429 R; 260/448.8 R; 560/55; 560/56; 560/100; 560/102; 562/490; 562/492; 562/496; 562/465; 562/466
[58] Field of Search .................. 560/105, 102, 55, 56, 560/100; 260/448.8 R

[56] References Cited

PUBLICATIONS

Taylor et al, J.A.C.S. 98, 6752 (1976).
McKillop et al, J.A.C.S. 95, 3340–3343 (1973).

Primary Examiner—Jane S. Myers
Attorney, Agent, or Firm—John T. Reynolds

[57] ABSTRACT

2-Aryl-$C_3$ to $C_6$-alkanoate esters are prepared economically by reacting an enol ether of an aryl alkyl ketone with a trivalent thallium salt in an organic solvent. The trivalent thallium ions can be regenerated by adding a peracid and a reactive form of manganese, ruthenium, cobalt, iridium, hafnium, osmium or neobium to oxidize monovalent thallium ions to the trivalent state, in a sequential, continuous or stoichiometric procedure. The ester intermediate product is then converted to the corresponding 2-aryl-$C_3$- to $C_6$-alkanoic acid or salt thereof. The aryl group is selected so the resulting acid product will be a useful compound such as anti-inflammatory, analgesic and anti-pyretic drug or agriculturally useful product. Examples of drug acids which can be made by this process include ibuprofen, flurbiprofen, fenoprofen and naproxen and the like.

14 Claims, No Drawings

PROCESS FOR PREPARING ARYLALKANOIC ACID DERIVATIVES

INTRODUCTION

This invention relates to chemical processes for preparing 2-arylalkanoic acid ester compounds. More particularly, this invention provides an improved process for preparing useful 2-aryl $C_3$ to $C_6$-alkanoate, and preferably 2-arylpropionate esters, and the resulting acids and salts thereof using trivalent thallium ions. This invention is particularly concerned with providing an improved process for regenerating the trivalent thallium ions used in the process.

BACKGROUND OF THE INVENTION

(a) 2-Arylalkanoic acids

A variety of 2-arylalkanoic acids are now known to be useful as active anti-inflammatory, analgesic and anti-pyretic pharmaceutical drug products. A few of the better known include the 2-arylpropionic acid derivatives such as fenoprofen which is 2-(3-phenoxyphenyl)-propionic acid and related compounds which are described in Marshall U.S. Pat. No. 3,600,437, ibuprofen which is 2-(4-isobutylphenyl)propionic acid and which is described with other related compounds in Nicholson et al. U.S. Pat. No. 3,385,886, naproxen which is 2-(6-methoxy-2-naphthyl)propionic acid which is described with other related compounds in Belgian Pat. No. 747,812 (Derwent Index No. 71729R-B). In addition a large variety of other 2-aryl-$C_3$ to $C_6$-alkanoic acid compounds are described in the medical, pharmaceutical and patent literature including the above patent references as well as Shen U.S. Pat. No. 3,624,142, and Adams et al., U.s. Pat. No. 3,793,457, which patents describe some fluoro-substituted biphenylalkanoic acids. Another compound of interest of this latter type is flurbiprofen which is 2-(2-fluoro-4-biphenylyl)propionic acid. Thus, a large variety of 2-aryl-$C_3$ to $C_6$-alkanoic acids, and particularly the 2-arylpropionic acid drug compounds are known and more of such compounds will undoubtedly be discovered and described in the future patent and other technical literature.

(b) Prior Processes

The above patent references also describe a variety of process routes for preparing useful 2-aryl-$C_2$ to $C_6$-alkanoic acids. However, some of the prior processes suffer a variety of disadvantages including expensive starting materials, dangerous by-products, and gross quantities of by-products necessitating substantial expense in destroying or getting rid of such by-products. As a result, chemists skilled in chemical process research continue to study and search for improved processes for making the more economically significant 2-aryl-$C_3$ to $C_6$-alkanoic acids, and particularly the 2-arylpropionic acids.

Among the possible process routes being explored to prepare the useful ester compounds are processes involving the use of trivalent thallium salts as reactants. A. McKillop et al. in the *Journal of the American Chemical Society* (JACS), 95 (1973) pp. 3340–3343 describe a process for preparing methyl arylacetates by the oxidative rearrangement of acetophenones with thallium (lll) nitrate (TTN). Treatment of acetophenone at room temperature with 1 equivalent of TTN in a mixture of methanol and 70% aqueous perchloric acid (5 to 1) resulted in smooth reduction of the TTN to thallium (I) nitrate; precipitation of the inorganic salt was complete after 5 hours. Filtration and evaporation of the filtrate gave an oil which by glpc analysis consisted of two components in the ratio of 16:1. They were identified as methyl phenylacetate (94%) and $\omega$-methoxyacetophenone (6%). Distillation of the mixture gave pure methyl phenylacetate in 84 percent yield. When this process was applied to the oxidation of propiophenone with TTN in acidic methanol, a mixture of products was obtained which consisted of methyl $\alpha$-methylphenyl acetate (45%) and $\alpha$-methoxypropiophenone (32%).

See also Chemical Abstracts, 82, (1975), page 501, item 16821x (abstracting Japan Kokai 74 48661) which refers to the production of 2-substituted benzothiazolacetic acid esters using perchloric acid-methanol mixtures. However, chemists and engineers concerned with designing large scale chemical processes would prefer to avoid process conditions which would involve the use of perchloric acid-methanol mixtures which are potentially hazardous or explosive.

E. C. Taylor and A. McKillop also disclosed a process for preparing methyl 2-phenylpropionate as the only substantial product by reacting propiophenone with anhydrous trivalent thallium trinitrate on a solid support at the April, 1974 American Chemical Society (ACS) meeting in Los Angeles and the IUPAC meeting in Belgium in August, 1974, respectively, and now in *J. Amer. Chem. Soc.*, 98, 6752 (1976). However, as is apparent from the above reports, working directly with the ketone reactant (here the propiophenone) and trivalent thallium salt in an aqueous organic medium results in a yield lowering mixture of products which chemical process chemists and engineers would prefer to avoid. Also, when the ketone is reacted directly with the anhydrous trivalent thallium salt on a solid support (TTN: support=1:2w/w), a large quantity of the inert support is required because the trivalent thallium salt supported thereon reacts mole for mole (stoichiometric proportions) with the ketone reactant. The reaction in commercial scale operation would thus produce huge quantities of monovalent thallium salt on solid support which must be handled or otherwise disposed of, thus inherently increasing the total cost of the process. Those skilled in the chemical process art continue to search for improved, technically practical, economical processes for preparing these valuable drug compounds, which would avoid the above problems.

Also, prior to this invention, inventors including the applicant herein have described and claimed in U.S. application Ser. No. 696,720, filed June 16, 1976, a process for preparing a 2-aryl-$C_2$ to $C_6$-alkanoate ester by reacting an enol ether with trivalent thallium ions in an organic liquid containing at least a minor amount of an alcohol, water or other nucleophile at a temperature of from about $-25°$ C. to about reflux temperature of the mixture for a time sufficient to form the 2-aryl-$C_2$ to $C_6$-alkanoate ester. However, as that process proceeds, the trivalent thallium ion content of the mixture is consumed as it reacts stoichiometrically with the enol ether content of the mixture and is converted to its reduced and oxidatively inactive monovalent thallium ion state.

The availability of a practical and economic method for regenerating the reactivity of the thallium ion content in these mixtures to obtain the desired quantities of the ester product would greatly extend the utility of this chemistry.

OBJECTS OF THE INVENTION

It is an object of this invention to provide an improved process for preparing 2-aryl-substituted $C_3$ to $C_6$-alkanoate esters, and the acids therefrom, based upon the use of trivalent thallium salts, which process minimizes the production of undesired yield-lowering by-products and potential hazards and eliminates the necessity for using inert, solid support materials for the thallium salt reactant to obtain substantially only the desired 2-arylalkanoate ester intermediate product.

It is a further object of this invention to provide an improved process for preparing 2-aryl-substituted $C_3$ to $C_6$-alkanoate esters which are useful as intermediates for preparing the corresponding 2-aryl-$C_3$ to $C_6$-alkanoic acids which are useful as the active ingredient in anti-inflammatory, analgesic and anti-pyretic pharmaceutical formulations, either per se or as a pharmaceutically acceptable salt thereof.

Another object of this invention is to provide an improved process for preparing 2-aryl-$C_3$ to $C_6$-alkanoate esters using trivalent thallium ions in a mild chemical continuous or semi-continuous manner involving the regeneration of trivalent thallium ions from monovalent thallium ions in a sequential, continuous or at least stoichiometric manner, using a per acid and various metallic compounds as oxidation promoters in a single reaction mixture or a cyclic process.

Other objects, aspects and advantages of this invention will be apparent to one skilled in this art from the description and claims which follow.

SUMMARY OF THE INVENTION

Briefly, according to this invention it has been found that in a process for preparing 2-aryl-substituted $C_3$ to $C_6$-alkanoate esters in high yields as substantially the only organic product by reacting an enol ether derivative of an aryl $C_2$ to $C_5$-alkyl ketone with a trivalent thallium salt in a one or two phase liquid medium containing at least one equivalent of an alcohol, water or other nucleophile, and after essential exhaustion of prior quantities of enol ether and trivalent thallium ions in the mixture, the process can be improved whereby the trivalent thallium ions needed for further reaction with enol ether are generated from a monovalent thallium salt of an organic carboxylic acid having a pKa above about 2, contained in the mixture by reacting the monovalent thallium ions with (a) a perorganic acid having a pKa above about 2 in an amount at least about stoichiometrically equivalent to the monovalent thallium content of the mixture, preferably a percarboxylic acid, in the presence of (b) a reactive form of a metal selected from the group consisting of at least one of manganese, ruthenium, cobalt, iridium, hafnium, osmium and neobium, said non-thallium reactive metal form being provided in a sufficiently soluble form to promote oxidation of monovalent thallium ions to the trivalent thallium valence state.

It has been discovered that when the thallium ion source is derived from salts of organic acids, which acids have a pKa greater than 2, preferably above 4, and after essential exhaustion of the first quantities of either of the enol ether or the trivalent thallium ion reactant in the mixture, the trivalent thallium ions can be regenerated by adding a peracid and a reactive form of manganese, ruthenium, cobalt, iridium, hafnium, osmium or neobium to oxidize the monovalent thallium ions to the trivalent state. Thereafter, upon further addition of enol ether, additional quantities of 2-aryl-$C_3$ to $C_6$-alkanoate ester are produced, while thus lowering the total amount of thallium material which must be handled in the process. The oxidation of the enol ether can be carried out in a two-phase system, e.g, a water/water immiscible organic liquid solvent mixture or an aqueous organic acid/immiscible organic liquid, e.g., aqueous acetic acid/hexane mixture. In such a system the regeneration of the trivalent thallium ions is carried out in the aqueous layer, possibly in another vessel, and then the trivalent thallium ion solution or suspension is returned to the enol ether reaction vessel for further reaction to form ester product. This mode of operating the process allows the enol ether oxidation/trivalent thallium ion regeneration process to be run in a continuous manner.

DETAILED DESCRIPTION OF THE INVENTION

More specifically, this invention provides an improved process for preparing 2-aryl-$C_3$ to $C_6$-alkanoate esters which involves the reaction of an enol ether of the formula

with trivalent thallium ions in an organic liquid medium containing at least one equivalent of an alcohol or water at a temperature of from about $-25°$ C. to about reflux temperature of the mixture for a time sufficient to form the 2-aryl-$C_3$ to $C_6$-alkanoate ester product

wherein Ar is the aromatic moiety of a useful acid product, containing from 6 to 13 carbon atoms, in which the aryl ring portion of the aromatic moiety is a phenyl, phenoxyphenyl, naphthyl or biphenylyl group bonded to the carbon atom adjacent to the carbonyl carbon atom (of the carboxylate ester product) at an aryl ring carbon; R in III above is $C_1$ to $C_6$-alkyl, benzyl, phenyl, tris ($C_1$ to $C_3$-alkyl)silyl or the like; R' is equal to R or is $C_1$ to $C_4$-alkyl, preferably methyl or ethyl, phenyl, or benzyl group derived from the solvent medium; and Y and Z denote the residue of the $C_3$ to $C_6$-alkyl moiety and each of Y and Z can be hydrogen or $C_1$ to $C_4$-alkyl, with Y and Z having a total of from one to 4 carbon atoms.

We prefer to prepare the enol ether reactant from a readily available ketone of the formula

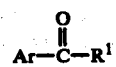

wherein Ar is defined above and $R^1$ is $-CH_2)_nH$ where n is 2 to 5 or $-CH(Y)Z$ wherein Y and Z are as defined above, through a ketal intermediate of the formula

wherein Ar, R and $R^1$ are as defined above, under substantially anhydrous, acidic conditions.

The reaction of the enol ether and the trivalent thallium ions to form the ester products of the process will proceed in a variety of solvents and solvent mixtures, e.g., in lower aliphatic $C_2$ to $C_6$-alkanols, liquid alkanoic acids or alcohol/alkanoic acid mixtures. This reaction can also be carried out in a two-phase system comprising the above types of alcoholic and acids combined with organic liquid solvents such as hydrocarbons, e.g., hexane, heptane and commercially available hydrocarbon solvent mixtures such as Skellysolve® B, and the like, or with chlorohydrocarbons, e.g., methylene chloride, chloroform, carbon tetrachloride, ethylene dichloride, and the like, or with liquid aromatic hydrocarbons, e.g., benzene, toluene, xylene.

This process can be used as part of an overall process to prepare a wide variety of useful aryl-$C_3$ to $C_6$-alkanoic acids. Acid products of immediate concern to us are those which have medicinal uses when compounded into appropriate pharmaceutical formulations and dosage forms. Examples of such compounds which can be made from this process include those wherein Ar is 3-phenoxyphenyl, $C_3$ to $C_5$-alkylphenyl, 4-biphenylyl substituted with up to 3 fluorine atoms on ring carbons thereof and 2-naphthyl substituted in the 6-position thereof with methoxy. Also, 2-phenyl $C_3$ to $C_6$-alkanoic acids such as 2-phenylpropionic acid, and 2-methyl-2-phenylpropionic acid and the like which have plant growth regulatory properties can also be prepared by the process of this invention.

Enol ether compounds (III) are sometimes formed as a mixture of stereoisomers, but the success of the process does not depend upon the isomer configuration or isomer ratio of enol ether, so the stereoconfigurations are not shown here, and such mixtures of enol ethers can be used in this process.

For use in this invention, the trivalent thallium ions are provided in the form of salts thereof with an organic carboxylic acid having a pKa above about 2 which will ionize under the reactant mole ratio, solvent and temperature reaction conditions to create an electrophilic thallium ion species in the mixture. It has been found according to this invention that these salts are the best thallium ion sources in a process wherein the trivalent thallium ions are to be regenerated in the reaction mixture or in a separate vessel for recycling back to the enol ether to ester reaction mixture for reuse in the process. Examples of organic acid salts of thallium for this purpose include those of the $C_1$ to $C_6$-alkanoic acids and the $C_1$ to $C_6$-haloalkanoic acids such as the acetate, propionate, isobutyrate, hexanoate, α-chloroacetate, α-bromoacetate, α-chloropropionate, α-bromopropionate, α-chlorobutyrate, as well as thallium benzoate, and the like. Thallium acetate salts are preferred for reasons of cost and availability.

Although the enol ether to ester reaction of this process will proceed to at least some extent at low temperatures, as low as about −25° C., and the reactants and products are stable enough to withstand reflux temperatures of the reaction mixtures at atmospheric pressure, temperature ranges of from about −10° to about 100° C. are sufficient and preferred. With some combination of reactants and solvents it may be desirable to conduct the reaction at elevated pressures to push the reactions to completion in shorter periods of time, but for most combinations of reactants atmospheric pressure is sufficient to complete the reaction is less than 10 hours. The aryl group on the enol ether starting material is selected to provide the resulting 2-aryl-$C_3$ to $C_6$-alkanoic acid product with useful properties, such as anti-inflammatory, analgesic and antipyretic drug properties or herbicidal, plant growth regulatory or other practically useful properties. The substituent on oxygen of the enol ether can be any group which will form a 2-aryl-$C_3$ to $C_6$-alkanoate ester and which ester group is easily removed by known procedures to form the corresponding 2-aryl-$C_3$ to $C_6$-alkanoic acid products. The process of this invention produced substantially only the 2-aryl-$C_3$ to $C_6$-alkanoate ester, thus bringing the practical yields closer to the theoretical yields, while avoiding the necessity for including any bulky, inert support materials for the thallium compound in the reaction mixture and also the necessity of acid catalysis.

The preferred enol ether starting materials are those having an aryl (Ar) group, which is common to useful drug acids and include, for example, 3-phenoxyphenyl, $C_3$ to $C_5$-alkylphenyl, 4-biphenylyl, 4-biphenylyl substituted with a total of up to about 3 fluorine atoms in the phenyl ring thereof, and 2-naphthyl substituted in the 6-position with methoxy and R is $C_1$ to $C_4$-alkyl, and $R^1$ is $C_2$ to $C_4$-alkyl. Useful compounds can also be made by the process of this invention where the aryl group is a simple unsubstituted phenyl, naphthyl or biphenylyl.

Ketones which can be used to prepare the enol ether starting materials for use in the process of this invention are known compounds or can be prepared by procedures known in the art. Examples include those of the formula

(IV)

wherein Ar denotes the aryl moiety in known arylalkanoic acid compounds, and includes those Ar groups described, for example, in Marshall U.S. Pat. No. 3,745,223, Marshall U.S. Pat. No. 3,600,437, the biphenylyl and substituted biphenylyl groups described in Shen U.S. Pat. No. 3,624,142, the fluoro-4-biphenylyl groups described in Adams et al., U.S. Pat. Nos. 3,793,457 and 3,755,427, 2-fluoro-4-biphenylyl, the 3,4-(disubstituted phenyl) groups described in Krausz et al. U.S. Pat. No. 3,876,800, and the 4-substituted phenyl groups described, for example, in Nicholson et al. U.S. Pat. No. 3,228,831 and the 6-substituted 2-naphthyl groups in Belgian Pat. No. 747,812, and $R^1$ is

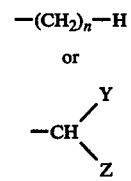

wherein n is 2 to 5, Y and Z are $C_1$ to $C_4$-alkyl or hydrogen with at least one of Y and Z being $C_1$ to $C_4$-alkyl. A preferred subgroup of ketones for use in preparing the ketals and enol ethers for use in the process of this invention are the aryl ethyl ketones, wherein the Ar group is as exemplified above. The most preferred ketones would be those which possess the Ar moieties which are of established economic interest for use in preparing the most useful and commercialized acid compounds, e.g., useful drug acid compounds. Examples of these ketones would be those ketones wherein Ar in the above formula IV is 4-isobutylphenyl, 4-phenoxyphenyl, 3-phenoxyphenyl, 2-fluoro-4-biphenylyl, 6-methoxynaphthyl, and $R^1$ is -$(CH_2)_n$H wherein n is 2 to 4.

Procedures for making the enol ether starting materials from the ketones for the process of this invention are known in the art. Examples of such procedures include:

(A) reaction of the selected ketone with a trialkyl orthoester such as trimethyl orthoformate in the presence of an acid catalyst such as sulfuric acid, methanolic hydrogen chloride, p-toluenesulfonic acid, ferric chloride or ammonium nitrate, styrene-divinylbenzene copolymer sulfonic acid resin materials such as those sold under tradenames or trademarks such as Amberlyst-15 (see "Amberlyst-15, Superior Catalyst for the Preparation of Enol Ethers and Acetals" by S. A. Patwardhan et al. in SYNTHESIS, May, 1974, pp. 348-349).

(B) reaction of the ketone with simple alcohols, preferably $C_1$ to $C_4$-alkanols, in the presence of an acid catalyst, including the use of sulfonic acid exchange resins such as the styrene/divinylbenzene copolymer sulfonic acid resins exemplified by Amberlyst-15 (Rohm & Haas Company, Philadelphia) and Dowex 50 (Dow Chemical Company, Midland, Michigan) at low temperature, e.g., −28° C., favors the formation of the ketone acetal (see *J. Org. Chem.*, Vol. 24, November, 1959, pp. 1731-1733, an article by N. B. Lorette et al., entitled "Preparation of Ketone Acetals from Linear Ketones and Alcohols").

(C) reaction of the selected ketone with acetone dimethyl acetal (2,2-dimethoxypropane) to effect transketalizaton, as described in an article entitled "Preparation of Ketals from 2,2-Dimethoxypropane" by N. B. Lorette et al. in *J. Org. Chem.*, Vol. 25, April, 1960, pp. 521-525.

(D) conversion of the corresponding ketal (acetal) to the enol ether by distillation over catalysts such as p-toluenesulfonic acid (see SYNTHESIS, supra).

For the preparation of the preferred aryl alkyl ketones, a Friedel-Crafts reaction can be used, e.g., to effect reaction according to the following general format

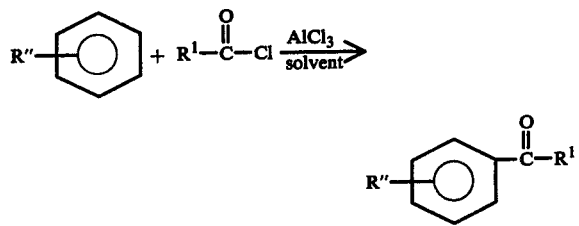

wherein R" is the residue of the desired aryl (Ar) group and $R^1$ is the residue of the carboxylic acyl halide. For example, the 6-methoxy-2-naphthyl propiophenone can be prepared by reacting 6-methoxynaphthalene with propionyl chloride in the presence of aluminum chloride in methylene chloride. The resulting 6-methoxy-2-naphthyl ethyl ketone is converted to the methyl enol ether starting material for this process by reacting it with trimethyl orthoformate in the presence of acid and heating in vacuo. The 3-phenoxyphenyl ethyl ketone methyl enol ether can be prepared by reacting 3-hydroxyphenyl ethyl ketone with phenyl bromide in the presence of potassium carbonate to form 3-phenoxyphenyl ethyl ketone and then reacting this ketone with trimethylorthoformate to form the ketal followed by heating with acid. The enol ether of 2-fluoro-4-biphenylyl ethyl ketone is formed by reacting 2-fluoro-4-biphenylyl ethyl ketone with trimethylorthoformate to form the ketal, then heating with p-toluenesulfonic acid in vacuo. The 2-fluoro-4-biphenylyl ethyl ketone can be prepared from 4-bromopropiophenone via 4'-bromo-3'-nitropropiophenone (See *Chemical Abstracts*, 61, p. 8232g), 4-propionyl-2-nitrobiphenyl (Ullman reaction), 4-propionyl-2-aminobiphenyl (reduction) and finally the Schiemann Reaction. See U.S. Patent No. 3,793,457, Example 1, for a similar synthesis of 2-fluoro-4-biphenylyl methyl ketone. The difluorobiphenyl ketone can be prepared by reacting 4-cyano-2,2'-difluorobiphenyl with ethyl magnesium bromide to form the difluoro biphenylyl ethyl ketone. See U.S. Pat. No. 3,755,427. This ketone can be converted to the enol ether by the procedure described above. A preferred method for preparing the enol ether for preparing ibuprofen esters according to this invention is set forth in the detailed examples below.

The rate of the reaction between the enol ether and the trivalent thallium ion source is affected by the solvent in which the reaction is run and the concentration of thallium ion in the reaction mixture. For example, the reaction of stoichiometric quantities of trivalent thallium acetate and the p-isobutylpropiophenone methyl enol ether in absolute methanol requires extended reaction times for good conversion to methyl 2-(p-isobutylphenyl)propionate. Reaction occurs rapidly in such mixtures to about 50%, and then the reaction rate slows dramatically. However, with the use of excess trivalent thallium acetate relative to the molar content of enol ether in the methanol mixture, this reaction was found to proceed rapidly or at slightly above room temperature. The rate of enol ether to ester product reaction is enhanced as the concentration of a $C_1$ to $C_6$-alkanoic acid, e.g., acetic acid (as co-solvent with methanol) increases. However, as the amount of alkanoic acid co-solvent increases, the rate of the competing enol ether hydrolyses reaction to form ketone or methoxy ketone by-products is increased. To minimize undesired competing reactions, I have found that the use of 80/20 v/v mixture of methanol/acetic acid or acetic acid/water solutions as solvent mixtures gave adequate enol ether to ester product reaction rates with only minor hydrolysis.

When the enol ether plus trivalent thallium ion reaction to form the ester product plus monovalent thallium ions reaction subsides or stops, that reaction mixture is treated according to the process of this invention to regenerate trivalent thallium ions which have become depleted in the reaction mixture. The monovalent thallium ions are oxidized back to the trivalent state, either in the same reaction mixture or in a separate vessel, by providing (a) a perorganic acid preferably a percarboxylic acid having a pKa above about 2 in an amount which is at least about stoichiometrically equivalent to the monovalent thallium content in the mixture in the presence of (b) a reactive form of a non-thallium metal selected from the group consisting of at least one of manganese, ruthenium, cobalt, iridium, hafnium, osmium and neobium, said non-thallium reactive metal form being provided in a sufficiently soluble form to promote oxidation of monovalent thallium ions to the trivalent thallium valence state. Generally, these promoter metals are placed in the thallium ion solution phase. The amount of manganese, ruthenium, cobalt, iridium, hafnium, osmium and neobium metal or compound thereof needed to catalyze the thallium oxidation is quite small. While less than 1% by weight of the non-thallium reactive metal compound, based on the weight of the thallium salt being treated, promotes the oxidation by the percarboxylic acid, it is preferred that from about 1% to about 10% by weight relative to the weight of the thallium salt present of the selected non-thallium metal compound catalyst be used.

Examples of useful forms of these manganese, ruthenium, cobalt, iridium, hafnium, osmium and neobium oxidation promoter elements include reactive salt forms thereof including the sulfate, halides, the organic acid salts, such as the salts thereof with $C_1$ to $C_6$-alkanoic acids, benzoic acid and the like, the oxides and hydroxides of such metals such as manganese oxide, manganese hydroxide, alkali metal, such as sodium, potassium, lithium and other forms of the permanganate ion, as well as organic/inorganic reactive forms of such metals, such as tris(triphenylphosphine)ruthenium dichloride or dibromide and the like. The preferred metal promoters for this reaction for reasons of reactivity and cost are the reactive forms of manganese, ruthenium and cobalt. Those which are less preferred are the reactive forms of iridium, hafnium, osmium and neobium, but they can be used under the proper conditions, including time, solvent choice, peracid choice, and the like.

I have found that of these metal promoter compounds, all of them work well in a $C_1$ to $C_{10}$-alkanoic acid or aqueous alkanoic acid, e.g., aqueous acetic acid, which contains enough alkanoic acid to prevent hydrolysis of thallium (III) alkanoate in the mixture to thallium (III) oxide, $Tl_2O_3$. Manganese compounds can also be used in organic liquid/aqueous systems such as $C_5$ to $C_{10}$-hydrocarbons free of aliphatic unsaturation or methanol or other liquid alcoholic solvents or alcohol/water solvent mixtures, including primary, secondary or tertiary alcohols and mixtures of these alcoholic solvents with water. Of the organic liquid media, ruthenium works in tert-alkanols but not so well in primary or secondary alcohol systems. Ruthenium and cobalt work best in $C_1$ to $C_{10}$-alkanoic acids or aqueous $C_1$ to $C_{10}$-alkanoic acids. The remaining metal promoter compounds work best in aqueous $C_1$ to $C_{10}$-alkanoic acid.

Manganese is the preferred thallium oxidation promoter catalyst. A preferred form of the manganese catalyst is divalent manganese diacetate, which is usually available as its tetrahydrate, although other forms of manganese may be used including manganese $C_1$ to $C_5$-alkanoate salts other than the manganese diacetate referred to above, manganese sulfate, manganese chloride or bromide, manganese dioxide, alkali metal permanganates, principally sodium, potassium and lithium permanganates, and the like.

The amount of peracid, e.g., a percarboxylic acid such as peracetic acid, used to oxidize monovalent thallium ions to the trivalent thallium ion state in the presence of the non-thallium oxidation promoter metal, e.g., manganese diacetate, is not critical since any excess peracid is rapidly decomposed to give a peracid-free solution of trivalent thallium alkanoate salt. The oxidation of the enol ether reactant by these trivalent thallium ion solutions was found to give the same product mixtures as obtained with commercially available trivalent thallium salts under similar conditions. However, I have found according to this invention that the use of percarboxylic acids, such as peracetic acid, for regeneration of trivalent thallium ions offers additional advantages. The methyl 2-(p-isobutylphenyl)propionate ester (ibuprofen ester) product was found to be relatively stable toward peracid. In fact, as indicated above, the oxidation of monovalent thallium acetate to trivalent thallium acetate with peracid could be carried out in the presence of the ibuprofen ester product with no apparent effect on the ester of the $Tl^+$ to $Tl^{+++}$ reaction. Thus, a sequential addition of peracid oxidant and enol ether reactant to a single reaction mixture, such that the peracid and enol ether are never present in solution simultaneously allows in situ regeneration of trivalent thallium ions and avoids peracid oxidation of the enol ether. Our studies have shown that peracetic acid solutions prepared using a sulfonic acid resin catalyst (as opposed to a soluble acid catalyst such as p-toluenesulfonic acid) are preferred if a large number of cycles of the process is to be carried out. The gradual buildup of strong acid, such as sulfuric acid which is present in some commercial grades of 40% peracetic acid solutions of p-toluenesulfonic acid, if it is used as a catalyst in peracid formations, was found to inhibit the $Tl^+$ to $Tl^{+++}$ oxidation reaction after a number of cycles. With sulfuric or sulfonic acid free peracid solutions, the enol ether plus trivalent thallium ion → ester product and $Tl^+$ to $Tl^{+++}$ oxidation reactions proceed readily even after a large number of cycles.

In one mode of conducting the process of this invention, the trivalent thallium ions are regenerated from monovalent thallium ions in the enol ether reaction mixture by providing the peracid to the monovalent thallium ion containing enol ether deficient mixture in the presence of a reactive form of manganese, ruthenium, cobalt, iridium, hafnium, osmium or neobium, preferably a reactive form of manganese or ruthenium. In another mode of the process, the liquid phase containing all or most of the thallium ion content is separated from the liquid phase containing all or most of the enol ether and ester materials, and the aqueous thallium ion phase is treated with an effective amount of a perorganic acid as described above in the presence of one or more of the oxidation promoter metals to oxidize the monovalent thallium ions to the trivalent thallium valence state and then the resulting liquid phase containing the trivalent thallium ion rich phase is returned for admixture with the liquid phase containing the enol ether for conversion thereof to the respective ester product.

To produce larger quantities o the 2-aryl-$C_3$ to $C_6$-alkanoate esters in the same reaction vessel or in a continuous manner when thallium salts derived from organic acids having a pKa of 2 or higher are used, I have discovered that after essential exhaustion of the first or prior quantities of enol ether in the mixture the trivalent thallium ions needed for further reaction with enol ether can be generated from monovalent thallium ions either contained in that reaction mixture or in a separate vessel by providing or otherwise mixing with the monovalent thallium ion containing mixture at least about a stoichiometric amount, preferably a slight excess, of a peracid derived from an organic carboxylic acid having a pKa about 2 or above in the presence of a reactive form of, preferably salt, oxide or base form of a metal selected from the group consisting of at least one of manganese, ruthenium, cobalt, iridium, hafnium, osmium and neobium, said non-thallium metal, salt, oxide or base being provided in a form and concentration, either in the reaction medium or the separate reaction vessel to promote oxidation of monovalent thallium ions to the trivalent thallium valence state. Thereafter the regenerated trivalent thallium ion can be recombined with enol ether, either by adding additional enol ether to the same reaction vessel or by moving and adding the regenerated trivalent thallium ion mixture to the reaction vessel which contains more enol ether with which to react to form the additional 2-aryl-$C_3$ to $C_6$-alkanoate ester. This in situ generation or regeneration of thallium (III) ions from thallium (I) ions allows thallium (III) organic acid salts to be used in an essentially catalytic manner. The utility of these highly toxic thallium compounds is, thus, greatly extended and the hazards of working with them are greatly reduced. Peracetic acid, which is free of strong acids such as sulfuric acid, is preferred for use in this process. Commercial 40% peracetic acid contains about 1% sulfuric acid. We prefer preparing the peracid with a commercially available sulfonic acid ion-exchange resin which can be removed by filtration before use of the resulting peracid solution in this process. Alternatively, p-toluenesulfonic acid can be used to generate the peracid for use in this process.

When the enol ether to ester product reaction is completed or has proceeded to the optimum degree, the ester mixture can be separated from the thallium ion liquid phase, allowed to stabilize to room temperature, and the ester intermediate product recovered from the reaction mixture by conventional procedures. For example, water and a water-immiscible organic solvent can be added. The organic and aqueous phases can be separated and the organic phase containing the ester product can be dried by conventional means, e.g., over sodium sulfate. Removal of the organic solvent from the product ester can be accomplished by vacuum distillation of the solvent which leaves the ester as a residue, which can be further purified by conventional means or the residue can be treated directly to convert the ester to the corresponding 2-aryl-$C_3$ to $C_6$-alkanoic acid product.

In a two-phase system, the organic layer is isolated, washed with water, and concentrated to leave as residue the crude ester product. The aqueous phase containing the thallic salt is then recycled.

The ester intermediate product can be hydrolyzed or otherwise converted to the corresponding acid by conventional means. For example, the ester can be heated with reflux with a mixed aqueous/alcoholic solution of alkali metal hydroxide until the acid is formed, say for 0.5 to 3 hours. On cooling, the reaction mixture can be treated to recover the acid product, e.g., by washing the hydrolyzed reaction mixture with water, extracting with hexane or commercial mixtures of hexanes (e.g., Skellysolve ®B), to remove organic solubles, and the aqueous phase acidified and extracted with hexane. The extracts containing the acid product can be washed with aqueous salt solutions and dried. Thereafter, removal of the solvent by vacuum distillation leaves a crystalline acid product or an oil which crystallizes upon standing.

Preferred embodiments of the process of this invention include the preparation of any of the included ester products using thallium salts of a $C_1$ to $C_{10}$-alkanoic acid, preferably of acetic acid, in an organic liquid mixture containing aqueous alkanoic acid to effect enol ether conversion to the ester products. I have discovered that when these thallium alkanoate salts are used in such a common ion alkanoic acid solvent, the non-thallium reactive metal compounds, particularly manganese and ruthenium, readily promote the re-oxidation of monovalent thallium ions to the trivalent thallium state. The manganese and ruthenium can also be provided as the acetate or other alkanoate salt thereof. Peracetic acid is the preferred oxidizing acid for use with the acetate salts of the metals in aqueous acetic acid solutions thereof. The process can preferably include the use of a two-phase liquid system comprising aqueous $C_1$ to $C_{10}$-alkanoic acid as one phase to contain the bulk of the thallium and non-thallium oxidation promoter metal compounds, e.g., manganese or ruthenium acetates, and a $C_5$ to $C_{10}$-hydrocarbon free of aliphatic unsaturation as the other liquid phase to contain the bulk of the enol ether reactant and ester product. Examples of such $C_5$ to $C_{10}$-hydrocarbon solvents include pentane, hexane, heptane, octane, decane, benzene, toluene, xylene, norcarane, norpinane, norbornane, and mixtures thereof, including commercial mixtures such as Skellysolve ®B, and the like. This process is particularly well adapted for preparing $C_1$ to $C_6$-alkyl esters of ibuprofen by reacting a 4-isobutylpropiophenone $C_1$ to $C_6$-alkyl enol ether with trivalent thallium ions in a water-immiscible organic liquid mixture containing an aqueous $C_1$ to $C_{10}$-alkanoic acid, preferably aqueous acetic acid in which the trivalent thallium ions consumed in the enol ether conversion reaction are regenerated in a separated aqueous acid phase by reacting monovalent thallium ions resulting from that reaction with a percarboxylic acid having a pKa above about 2 in an amount at least stoichiometrically equivalent to the monovalent thallium ion content of the mixture in the presence of a reactive form of manganese, ruthenium cobalt, iridium, hafnium, osmium and/or neobium, preferably manganese or ruthenium, said non-thallium reactive metal being provided in a sufficiently aqueous acid soluble form, preferably as their acetate salts, and in amounts to promote or catalyze the oxidation of monovalent thallium ions to the trivalent thallium valence state, for re-use of the trivalent thallium ions to react with additional enol ether reactant.

The invention is further described and exemplified by the detailed examples which follow, but they are not intended to limit the scope of the invention.

Preparation 1

To a solution of 3.4 gm. (8.92 millimoles) of commercially available thallium triacetate [$Tl(C_2H_3O_2)_3$] in 25 ml. of absolute methanol stirred at room temperature under nitrogen in a 100 ml. round bottom flask, there was added 1.74 gm. (8.53 millimoles) of crude 4'-isobutyl-propiophenone methyl ether (enol ether) of the formula

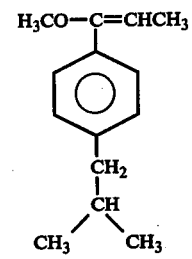

The resulting colorless solution was stirred for twenty-four hours, after which time gas liquid chromatography (glc) analysis of a sample of the reaction mixture indicated that about 95 percent of the enol ether reacted. The resulting reaction mixture was concentrated in vacuo to give a yellow viscous oil which was triturated with hexane and filtered. The resulting hexane solution was washed with aqueous saturated sodium chloride solution and, after separation from the aqueous phase, the hexane solvent was removed in vacuo to give 1.9 gm. of methyl 2-(4-isobutylphenyl)propionate as a pale yellow oil. By glc analysis the oil was about 85 percent pure 2-(4-isobutylphenyl)propionic acid (ibuprofen) methyl ester. NMR analysis of the oil confirmed that the ibuprofen methyl ester was the major product. The crude ester was hydrolyzed as described in the previous example to give 910 mg. of ibuprofen, after recrystallization.

EXAMPLE 1

(a) Using Methanol/Acetic Acid Mixture

To a solution of 260 mg. (1.0 mmole) of thallium (I) acetate and about 2 mg. of hydrated manganese diacetate in 4 ml. of methanol and 0.5 ml. of acetic acid there was added, while stirring, 0.4 ml. (2.7 mmole) of 41 percent peracetic acid solution in acetic acid. After thirty minutes of stirring to insure complete reaction to convert thallium (I) to thallium (III) in the mixture, there was added 200 mg. (1.0 mmole) of 4'-isobutylpropiophenone methyl ether (see structure in Preparation I) and the mixture was stirred for 1.5 hours. Gas liquid chromatographic analysis (glc) of a sample of the reaction mixture indicated that about 69 percent of the enol ether had been converted to methyl 2-(4-isobutylphenyl)propionate (ibuprofen methyl ester), based on the starting enol ether. This ester can be used to make ibuprofen therefrom.

(b) Using Aqueous Acetic Acid/Hexane

To a solution of 260 mg. (1.0 mmole) of thallium (I) acetate and 24 mg. (0.1 mmole) of hydrated manganese diacetate in 3 ml. of 80 percent aqueous acetic acid and 4.5 ml. of hexane, there was added 0.3 ml. (about 2.0 mmole) of 42 percent peracetic acid solution in acetic acid. After five minutes of stirring there was added 100 mg. (0.5 mmole) of 4-isobutylpropiophenone methyl enol ether in 0.5 ml. of hexane. After stirring the mixture for about thirty-five minutes, a glc analysis of a sample of the reaction mixture indicated that about 89 percent of the enol ether had been converted to methyl 2-(4-isobutylphenyl)propionate, based on the starting enol ether.

In the above procedure, manganese diacetate can be replaced by a variety of other manganese salts including manganese (II) 2,4-pentanedionate, manganese (III) 2,4-pentanedionate, manganese triacetate, manganese dioxide, manganese sulfate, manganese dichloride and potassium permanganate to obtain oxidation of thallium (I) ions to thallium (III) ions.

EXAMPLE 2

In Situ Regeneration of Thallium (III) Ions

In a 100 ml. 3-necked round bottomed flask with an addition funnel and a reflux condenser there was placed 1.5 g. (5.8 mmole) of thallium (I) acetate, 120 mg. (0.5 mmole) of hydrated manganese diacetate and 15 ml. of acetic acid. The mixture was stirred slowly while 1.5 ml. (10 mmole) of 42 percent practic acid in acetic acid solution followed by 25 ml. of hexane was added. The mixture was placed in a 50° C. bath. A 5.0 gm. (2.4 mmole) portion of 4'-isobutylpropiophenone methyl enol ether in about 5 ml. of methanol was placed in the addition funnel. Then one ml. of the enol ether solution, about 500 mg. of the enol ether, was added to the reaction flask from the addition funnel, to form methyl 2-(4-isobutylphenyl)propionate in the mixture.

When the addition of the enol ether was completed and after about three minutes of stirring 0.5 ml. (3.3 mmole) of 42 percent peracetic acid solution was added to effect oxidation of thallium (I) ions in the mixture to the thallium (III) ion state, followed in two minutes by another 1 ml. of enol ether solution to effect formation of more methyl 2-(4-isobutylphenyl)propionate ester in the mixture. This sequential addition of peracetic acid solution and enol ether was continued until addition of the enol ether in the addition funnel was completed. A glc analysis of a sample of the reaction mixture indicated that about 81 percent of methyl 2-(4-isobutylphenyl)-propionate ester (ibuprofen methyl ester) had been formed in this manner, based on the enol ether, from the in situ regenerated thallium (III) ions in the mixture.

The reaction mixture was cooled to room temperature and diluted with about 30 ml. of water. The organic layer was removed and the aqueous layer was extracted with four portions of hexane. The combined hexane extracts were washed with water and concentrated in vacuo to give about 5.0 gm. of a yellow oil. This oil product was dissolved in a mixture of 17 ml. of methanol and 25 ml. of hexane. The resulting solution was treated with 6.5 gm. of 50 percent aqueous sodium hydroxide solution for 1 hour at about 60° C. The mixture was cooled to room temperature, and then 50 ml. of 1 N aqueous sodium hydroxide and 50 ml. of hexane were added and the organic and aqueous layers were allowed to separate. The aqueous layer was acidified with 50 percent aqueous sulfuric acid and then extracted three times with hexane. The hexane extracts were washed with water, dried over sodium sulfate and concentrated in vacuo to give 4.0 gm., about 81 percent weight yield, of 2-(4-isobutylphenyl)propionic acid, now known generically as ibuprofen. Crystallization of the ibuprofen product from hexane gave 3.4 gm., 67 percent yield of ibuprofen. The amount of thallium (I) acetate used was about 23 percent of the stoichiometrically required amount based on the enol ether consumed.

EXAMPLE 3

The enol ether to 2-aryl-$C_3$ to $C_6$-alkanoate and thallium (I) to thallium (III) ion regeneration process can also be conducted in a continuous manner using a known type of liquid-liquid extraction column reaction apparatus. Thus, for example, such a column can be operated in a counter-current or co-current mode with a solution of thallium (III) acetate in aqueous acetic acid being charged as one stream. A second stream of a solution of 4-isobutylpropiophenone methyl enol ether in a water immiscible hydrocarbon such as hexane or heptane is pumped into the column to mix and react with the thallium (III) ion content of the aqueous mixture. The flow of the aqueous acetic acid solution and the hydrocarbon phases are controlled so that phase separation and reaction can take place in the counter-current or co-current column. The temperature of the reaction mixture can be controlled to the desired range, say 0° to 100° C., by the use of heating jackets around the counter-current column or by other equivalent means. The time needed for the conversion of the enol ether to the ester product is quite short, as can be seen from Example 2, so that the reaction contact time or residence time of the liquids in the column can be readily controlled by controlling the flow of the reactant fluids into and out of the column.

The aqueous acetic acid phase rich in thallium (I) ions can be withdrawn from the bottom of the column and piped to a separate vessel where it is contacted with peracetic acid solution in the presence of one of the above-mentioned metal promoter compounds, e.g., manganese acetate, to oxidize the thallium (I) ions in the mixture to the thallium (III) valence state, and this resulting thallium (III) rich solution in aqueous acetic acid can be pumped back to the primary counter-current or co-current column or Backmix reactor for further reaction with enol ether to form additional quantities of the 2-aryl-$C_3$ to $C_6$-alkanoate ester product.

The hydrocarbon phase containing the 2-aryl-$C_3$ to $C_6$-alkanoate ester product in a counter-current column can be drawn off the top of the column and piped to an appropriate vessel for separation from the hydrocarbon phase, purification and conversion to the corresponding 2-aryl-$C_3$ to $C_6$-alkanoic acid, as described above. The hydrocarbon solvent can be recycled to dissolve more enol ether reactant for reaction in the counter-current column with thallium (III) ions therein.

Literature descriptions of suitable liquid-liquid counter-current/co-current column extractors can be found, e.g., in E. G. Scheibel, AIChEJ, Vol. 2(1), March 1956 Coulson and Richardson, "Chemical Engineering," pages 748–774, Pergamon Press Ltd., London (1967).

EXAMPLE 4

In a 25 ml. vial was placed 260 mg. (1.0 millimole) of thallium (I) acetate and 4 ml. of glacial acetic acid. With stirring there was added 0.2 ml. of 40% peracetic acid in acetic acid (commercial) followed by a few milligrams of tris(triphenylphosphine)ruthenium dichloride. After 2 hours of stirring this mixture 200 mg. (1.0 mmole) of 4-isobutylpropiophenone methyl enol ether was added neat and the resulting mixture was stirred for 30 minutes. Analysis of the mixture by gas liquid chromatography (glc) methods indicated that about 50% of methyl 2-(4-isobutylphenyl)propionate had been formed based on the starting enol ether.

Similar results were obtained with ruthenium trichloride and ruthenium dioxide. Under the same reaction conditions hafnium tetrachloride, osmium tetroxide, neobium pentachloride, cobalt (II) 2,4-pentanedionate and cobalt (III) 2,4-pentanedionate were found to be less effective catalysts for the oxidation of thallium (I) to thallium (III) acetate but were effective to give methyl 2-(4-isobutylphenyl)propionate in varying amounts.

EXAMPLE 5

Following the procedure of Example 2, the enol ether of the formula

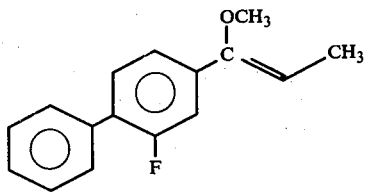

is reacted with thallium (III) acetate in an aqueous acetic acid/hexane mixture at 25° to 50° C. until methyl 2-(2-fluoro-4-biphenylyl)propionate is formed. This ester is isolated from the reaction mixture and hydrolyzed to 2-(2-fluoro-4-biphenylyl)propionic acid (generic name, flurbiprofen) by the described procedure.

In the same manner, the methyl enol ethers of (a) 6-methoxy-2-naphthyl ethyl ketone, (b) 3-phenoxypropiophenone and (c) p-chloropropiophenone are converted respectively to their corresponding 2-arylpropionate esters, namely to (a) methyl 2-(6-methoxy-2-naphthyl)propionate [which can be hydrolyzed to the acid 2-(6-methoxy-2-naphthyl)propionic acid, known generically as naproxen]; (b) methyl 2-(3-phenoxyphenyl)propionate [which can be hydrolyzed to the acid 2-(3-phenoxyphenyl)-propionic acid, known generically as fenoprofen]; and (c) methyl 2-(4-chlorophenyl)propionate, which can be hydrolyzed to the acid, 2-(4-chlorophenyl)propionic acid, a known acid.

EXAMPLE 6

Following the procedure of Example 1, the enol ether of isobutyrophenone of the formula

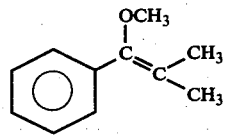

is reacted with thallium (III) acetate to give methyl 2-methyl-2-phenylpropionate. This ester is hydrolyzed to yield 2-methyl-2-phenylpropionic acid.

In a similar manner, the methyl enol ether of 3,4-dichloropropiophenone is converted to methyl 2-(3,4-dichlorophenyl)propionate. This ester is hydrolyzed to the acid, 2-(3,4-dichlorophenyl)propionic acid, which is a known acid having agriculturally significant, weed killing properties.

EXAMPLE 7

Preparation of Ibuprofen via isobutylpropiophenone methyl enol ether starting from p-isobutylbenzene A. Preparation of p-Isobutylpropiophenone In a 500 ml. 3-necked, round bottomed flask there was placed 25.50 ml. (40.14 g., 0.29 mmole) of phosphorus trichloride and 43.65 ml. (43.34 g., 0.58 mmole) of propionic acid. This mixture was stirred for 2.25 hours under nitrogen atmosphere at room temperature to prepare the propionyl chloride. By NMR propionyl chloride formation was complete in about 1.5 hours. Then 80 ml. of anhydrous methylene chloride was added and the resulting solution was cooled to about −5° C. (an ice-methanol bath). While stirring the cooled mixture, 87.50 g. (0.66 mmole) of aluminum chloride (technical grade) was added. After 10 minutes of stirring, 67.11 g. (0.50 mmole) of isobutylbenzene was added dropwise from an addition funnel over 55 minutes while maintaining the temperature of the mixture at about 0° to 5° C. The isobutylbenzene was about 99.6% pure and contained about 0.3% n-butylbenzene. The mixture was stirred for an additional 1.25 hours to insure as complete a reaction as possible and then poured into a solution of 250 ml. of ice water and 150 ml. of concentrated hydrochloric acid with vigorous stirring. The Friedal-Crafts reaction was complete in about 45 minutes under these conditions (by GLC analyses). The resulting mixture was extracted three times with 300 ml. portions of methylene chloride. The combined methylene chloride extracts were washed with 250 ml. of water and three times with 250 ml. of molar concentration aqueous sodium carbonate solution. The aqueous sodium carbonate extracts were back-extracted with 100 ml. of methylene chloride and the combined methylene chloride layers were dried over sodium sulfate. The dried methylene chloride solution was concentrated under vacuum to give crude p-isobutylpropiophenone as a pale yellow oil weighing 97.85 g. By GLC analyses, 3% methylene chloride was present. The chemical yield was about 95 g. or about 100% of theory.

B. Preparation of p-isobutylpropiophenone dimethyl ketal

To 11.33 g. (0.10 mole) of methyl acetimidate hydrochloride, prepared by known procedures, in a 100 ml. 3-necked, round-bottomed flask there was added a solution of 9.71 g. (actual 9.42 g.; 49.6 mmole) of crude p-isobutylpropiophenone, prepared as described in Part A above, in 23 ml. of absolute methanol. The resulting solution was stirred for 12 hours at room temperature to insure complete reaction. Gas liquid chromatographic analysis (Glc analysis) of an aliquot of the reaction mixture indicated greater than 99% ketal formation. The resulting mixture was filtered to remove the precipitated ammonium chloride and concentrated under vacuum. Hexane (50 ml.) was added to the residue and the resulting solution was again filtered to remove any acetamide which might be present. Removal of the hexane solvent under vacuum gave p-isobutylpropiophenone dimethyl ketal as a pale yellow oil which was used without further purification. The NMR was in accord.

C. Preparation of 1-(p-isobutylphenyl)-1-methoxy propene (also named p-isobutylpropiophenone methyl enol ether)

In a 100 ml. round-bottomed flask there was placed the crude p-isobutylpropiophenone dimethyl ketal, prepared from 49.6 mmole of crude p-isobutylpropiophenone by the procedure described hereinabove, and 3.0 g. (56.1 mmole) of anhydrous, finely ground ammonium chloride which had been dried under vacuum. Under vacuum (60 mm. Hg.) the mixture was heated with vigorous stirring to 130°–135° C. The pressure was then reduced to 6 to 8 mm. and the mixture was maintained at 130°–135° C. for 3 hours. On cooling, the ammonium chloride was removed by filtration under nitrogen and the solids were washed with 10 ml. of hexane. Concentration of the filtrate under vacuum gave 10.6 g. of a pale yellow oil. By NMR analyses (internal standard nitromethane) the oil consisted of 89.5% of the p-isobutylpropiophenone methyl enol ether and 5% of the p-isobutylpropiophenone dimethyl ketal. It was used without further purification. The overall chemical yield was 9.57 g. (94.6% of theory).

D. Preparation of Ibuprofen via methyl 2-(p-isobutylphenyl)propionate from the p-isobutylpropiophenone methyl enol ether In a 500 ml., 3-necked round-bottomed flask (Morton type) fitted with a mechanical stirrer, a reflux condenser and a thermometer there was placed 39.45 g. (150 mmole) of thallium acetate, 2.8 g. (4.1 mmole) of manganese diacetate.tetrahydrate, 40 ml. of distilled water and 160 ml. of glacial acetic acid. While stirring the resulting mixture there was added about 6 ml. of 41% peracetic acid solution. [The peracetic acid solution was prepared from 60 ml. of glacial acetic acid, 19 ml. of 90% hydrogen peroxide solution and 2.5 g. of a sulfonated polymer resin (Dowex MSC-1-H)]. Once the resulting solution turned dark brown, about 30 to 40 minutes at room temperature, an additional 33 ml. of 41% peracetic acid solution (for a total of about 39 ml., 300 mmole of peracetic acid) was added over about 5 minutes with ice bath cooling. This monovalent thallium oxidation reaction is quite exothermic. The temperature was maintained below 50° C. at all times. The resulting trivalent thallium ion containing solution was placed in an oil bath and the temperature was adjusted to 40° C. With vigorous stirring, a solution of 10.5 g. of crude p-isobutylpropiophenone methyl enol ether, prepared as described above, from 49.7 mmole of crude p-isobutylpropiophenone in 50 ml. of hexane was added via the addition funnel as rapidly as possible. The oxidative rearrangement of the enol ether reaction is exothermic. A 5° C. temperature rise was noted. A glc analysis of an aliquot sample of the reaction mixture after 3 minutes indicated reaction was complete. In other similar runs the reaction time was found to be less than 30 seconds under these conditions. After 17 minutes stirring was discontinued and the mixture was rapidly cooled to 10° C. Upon transfer to a separatory funnel, the hexane layer was removed and the aqueous acetic acid layer was extracted three times with 100 ml. portions of hexane. Hexane extracted essentially all of the desired products (enol ether reactant and ibuprofen ester) from the 80% acetic acid in water acid layer. Dilution of the aqueous acid layer followed by extraction with hexane gave only 160 mg. of additional material which consisted of polar oxidation products such as α-hydroxy-p-isobutylpropiophenone. The combined hexane extracts were washed with three 100-ml. portions of distilled water, 50 ml. of saturated sodium bicarbonate solution, and 50 ml. of saturated sodium sulfate solution. After drying the hexane fraction over sodium sulfate, the dried hexane fraction was concentrated under vacuum to 10.28 g. of crude methyl ibuprofen ester product as a pale yellow oil. By NMR (internal standardnitromethane) this pale yellow oil contained 90.2% of methyl ibuprofen ester and about 8% p-isobutylpropiophenone, for an overall yield of 9.27 g. (86.6% of theory).

E. Preparation of Ibuprofen from the ester

A 5.11 g. portion of the crude ibuprofen methyl ester prepared as described above was dissolved in 20 ml. of hexane and 12 ml. of methanol and cooled to 0° to 5° C. Then 6.0 g. (75 mmole) of a 50% sodium hydroxide solution was added and the resulting mixture was heated under reflux for 2 hours. On cooling, the mixture was transferred to a separatory funnel with about 50 ml. of 1N sodium hydroxide solution and hexane. The hexane layer was extracted with about 10 ml. of 1N aqueous sodium hydroxide and the combined aqueous layer was extracted with 50 ml. of fresh hexane. The neutral fraction isolated from the combined hexane extracts consisted primarily of p-isobutylpropiophenone. The aqueous layer was acidified with 50% aqueous sulfuric acid and extracted 3 times with 50 ml. portions of hexane. The combined hexane extracts were washed 3 times with 50 ml. portions of water and dried over sodium sulfate. Removal of solvent by vacuum evaporation gave crude ibuprofen as a pale yellow solid, weighing 4.20 g., having a purity of 96.7% by Glc analysis, again the impurities being about 1.4% p-isobutylbenzoic acid and 1.1% of the meta isomer of ibuprofen. The crude yield was 80.8% of theory. Recrystallization of the crude ibuprofen from hexane (2 ml./g.) gave 3.44 g. (70.3% chemical yield) ibuprofen.

EXAMPLE 8

Conducting Process in Continuous Manner Using a Scheibel Column

This example demonstrates a series of continuous runs of the process involving reaction between the enol ether (I) (4-isobutylpropiophenone methyl ether), in hexane and trivalent thallium acetate and manganese acetate in an acetic acid-water phase in a continuous apparatus system including a Scheibel column with auxiliary equipment, e.g., pumps, containers, purge tanks, and the like. Scheibel columns are well known in the chemical engineering field. See, e.g., Bulletin No. 33 (1963) of the York Process Equipment Company, 42 Intervale Road, Parsippany, New Jersey, 07054; and "Semicommercial Multistate Extraction Column, Performance Characteristics" by Edward G. Scheibel et al. in *Industrial and Engineering Chemistry*, Vol. 42, No. 6, pp. 1048 et seq.

The two input liquid phase feed compsitions were: (1) an 80% acetic acid in water solution containing 20% w/v trivalent thallium acetate and about 2.7% of divalent manganese diacetate based on the thallium salt content, introduced near the top of the Scheibel column, and (2) hexane containing 20% enol ether reactant introduced near the bottom of the column. The flow rates of the aqueous and hexane phases are adjusted to provide contact in the Scheibel column reactor between the enol ether and thallium ions in a ratio of about 2 molar equivalents of trivalent thallium ions per molar equivalent of enol ether.

The output compositions of the enol ether reactant stream (light phase) are set forth in the table below. A preliminary study of the hydrodynamics (hold up and flood rates) of the system including the Scheibel column was made with pure solvents (blanks) before experimenting with the thallium and enol ether solutions. The experimental conditions were varied from run to run to learn how to maximize the conversion of enol ether to ester product by (1) altering the residence time of the enol ether solution in the column (decreasing or increasing the light phase flow), and/or (2) providing increased mixing efficiency by simultaneously increasing the total throughput in the column and agitator speed (Scheibel, 1956). From the table below it can be seen that the amount of hydrolysis (or by-product ketone formation from the enol ether) is not significant compared to a sequential or batch operation of the process, where usually 5% to 10% of the enol ether reactant is converted to the ketone by-product per batch or sequence. This reduced ketone by-product production in the continuous process is due to the faster reaction rate between the enol ether and the trivalent thallium ions, the low residence time of the enol ether in the Scheibel column reactor part of the system and the relatively slow hydrolysis rate of the enol ether reactant to the undesired ketone by-products.

Since the oxidation of the thallium acetate by peracetic acid is done outside of the main Scheibel column reaction chamber, there are no significant amounts of oxidized by-products, e.g., p-isobutylbenzoic acid.

When the heavier thallium ion/manganese ion acetic acid solution phase drains from the Scheibel column, it contains monovalent thallium acetate, trivalent thallium acetate and manganese diacetate which manganese salt passes through the Scheibel column without reaction. The heavier solution is transferred to a mixing tank where it is reacted with a 40% to 42% peracetic acid solution prepared using p-toluenesulfonic acid or a sulfonated resin bead catalyst for a few minutes (5 to 10 minutes) to effect oxidation of the monovalent thallium ions in the solution mixture in the presence of the manganese acetate catalyst to the trivalent thallium ion state, while by-product oxygen gas is removed from the mixing tank. Thereafter the heavy phase containing the trivalent thallium ions, manganese diacetate in acetic acid/water solution can be concentrated or diluted with acetic acid and water to adjust the concentration of the thallium ions to the desired level before re-introduction of the heavy phase into the Scheibel column reactor for further reaction with enol ether in the lighter hexane phase.

A rough calculation shows that for a 100 kg./day of ibuprofen production a Scheibel column reactor being 0.75 m. long × 0.15 m. internal diameter can handle about 100 liters/hour total liquid flow. In this process the degree of mixing in the Scheibel column reactor has been found to be influential in experimental runs to shorten or lengthen residence times.

In these runs (see Table below) the hold-up of the thallium ion phase (heavy phase) in the column is about 75% of the column volume. Applied to the production scale of 100 kg./day of ibuprofen, using the same amount of thallium acetate (required in the enol ether reaction) as indicated above for circulation in the remaining parts of the continuous loop of the apparatus system, the total thallium acetate in the continuous system would be about 5 kg. of thallium acetate, an order of magnitude lower than the amount of thallium ions needed for the sequential operation and about two orders of magnitude lower than that needed for the batch operation.

A sample of the reaction mixture from run number 8 in the table below was worked up to convert the methyl 2-(4-isobutylphenyl)propionate ester product in the mixture to its acid, 2-(4-isobutylphenyl)propionic acid (generic name, ibuprofen). The sample was first washed with 80% acetic acid in water solution and hydrolyzed with sodium hydroxide and then crystallized out of hexane. The total conversion was found to be 63%. However, if correction is made for the unreacted enol ether (since the reaction conditions are not yet optimized and the reaction can be made to go to completion by changing the various parameters available in this system, e.g., flow rate and temperature); the overall conversion of the reacted enol ether is about 92%. This is quite consistent if one scans the column in the Table below showing weight percent of the products in the light liquid phase. The sum of the enol ether (unreacted) and the ibuprofen ester product is in the range of 92% to 97%. This means that with better optimization, it would be possible to achieve about 95 ± 3 percent conversion of the enol ether to isolated ibuprofen acid as compared to about 80 ± 5 percent conversion in the sequential or batch operation.

TABLE (A)

SUMMARY OF DATA FROM CONTINUOUS REACTION BETWEEN ENOL ETHER AND THALLIUM (III) ACETATE IN A SCHEIBEL COLUMN TO PRODUCE IBUPROFEN

| Expt No. | Light Phase Flow Rate (ml/min) (Enol Ether in Hexane) | Heavy Phase Flow Rate (ml/min) (Tl in 80% HOAc) | Stirring Rate (RPM) | Wt. % Product (G.C.) (Light Phase Output) | | | % Conversion of Enol Ether to Ibuprofen Methyl Ester (Chemical) Yield | % Enol Ether Converted to Ketone |
|---|---|---|---|---|---|---|---|---|
| | | | | Enol Ether | Ketone | Ibuprofen Methyl Ester | | |
| 1 | 8 | 5.5 | 80 | 78 | 8 | 14 | 13 | <1% |
| 2 | 8 | 3.4 | 80 | 84 | 6 | 10 | 7 | <1% |
| 3 | 5.8 | 7.8 | 325 | 80 | 7 | 13 | 11 | <1% |
| 4 | 5.8 | 13 | 325 | 77 | 8 | 15 | 14 | <1% |
| 5 | 3.7 | 18 | 425 | 68 | 8 | 24 | 24 | <1% |
| 6 | 3.7 | 24 | 425 | 52 | 9 | 39 | 42 | <1% |
| 7 | 3.7 | 24 | 590 | 39 | 8 | 53 | 57 | <1% |
| 8 | 3.7 | 36 | 590 | 29 | 7 | 64 | 68 | <1% |
| 9 | 2.2 | 50 | 590 | 18 | 5 | 77 | 80 | <1% |

| Expt No. | Isolated Product Ibuprofen Yield (Chemical) Based on Reacted Enol Ether Only | Based on Total Enol Ether Into Column | Additional Data |
|---|---|---|---|
| 1 | — | — | (a) No emulsion problems;.extremely good separation. |
| 2 | — | — | (b) Feed composition: % EE 90 % Ketone 8 % Ketal 1.5 % EE in Hexane phase 20 % Tl(OAc) in 80% HOAc phase 20 |
| 3 | — | — | |
| 4 | — | — | |
| 5 | — | — | (c) Hold up in column at end of expt. No. 9: Light Phase 85 ml. Heavy Phase 540 ml. |
| 6 | — | — | |
| 7 | — | — | (d) Temperature in Scheibel column 20° –25° |
| 8 | 92% | 63% | (e) HOAc is acetic acid EE is p-isobutylpropiophenone methyl ether Ketone is p-isobutylpropiophenone Ketal is p-isobutylpropiophenone dimethyl ketal |
| 9 | — | — | |

In the same manner, the methyl enol ethers of (a) 6-methoxy-2-naphthyl ethyl ketone, (b) 3-phenoxypropiophenone and (c) p-chloropropiophenone are converted respectively to their corresponding 2-arylpropionate esters, namely to (a) methyl 2-(6-methoxy-2-naphthyl)propionate [which can be hydrolyzed to the acid 2-(6-methoxy-2-naphthyl)propionic acid, known generically as naproxen]; (b) methyl 2-(3-phenoxyphenyl)propionate [which can be hydrolyzed to the acid 2-(3-phenoxyphenyl)propionic acid, known generically as fenoprofen]; and (c) methyl 2-(4-chlorophenyl)propionate, which can be hydrolyzed to the acid, 2-(4-chlorophenyl)propionic acid, a known acid.

In a similar manner, the methyl enol ether of 3,4-dichloropropiophenone is converted to methyl 2-(3,4-dichlorophenyl)propionate. This ester is hydrolyzed to the acid, 2-(3,4-dichlorophenyl)propionic acid, which is a known acid having agriculturally significant, weed killing properties.

We claim:

1. In a process which comprises reacting an enol ether of the formula

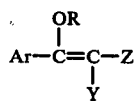
(III)

with trivalent thallium ions in an organic liquid containing at least one equivalent of an alcohol or water at a temperature of from about −25° C. to about reflux temperature of the mixture for a time sufficient to form a 2-aryl-$C_3$ to $C_6$-alkanoate ester of the formula

(I)

wherein in each formula Ar is the aromatic moiety of a useful acid product containing from 6 to 13 carbon atoms, in which the aryl ring portion of the aromatic moiety is a phenyl, phenoxyphenyl, naphthyl or biphenylyl group bonded to the carbon atom adjacent to the carboxyl ester moiety at an aryl ring carbon;

R is $C_1$ to $C_4$-alkyl, benzyl, phenyl, tris-($C_1$ to $C_3$-alkyl)silyl; and R' is equal to R or is an alkyl, benzyl, or phenyl group derived from the solvent medium;

Y and Z denote the residue of a $C_3$ to $C_6$-alkanoic acid moiety with each of Y and Z being hydrogen or $C_1$ to $C_4$-alkyl, with Y and Z having a total of from one to 4 carbon atoms, the improvement wherein the trivalent thallium ions needed for further reaction with enol ether are generated from a monovalent thallium salt of an organic carboxylic acid having a pKa above about 2, contained in the mixture, by providing (a) a perorganic acid having a pKa above about 2 in an amount at least about stoichiometrically equivalent to the monovalent thallium content in the mixture in the presence of (b) a reactive form of a metal selected from the group consisting of at least one of manganese, ruthenium, cobalt, iridium, hafnium, osmium and neobium, said non-thallium reactive metal form being provided in a sufficiently soluble form and in an amount sufficient to promote oxidation of monovalent thallium ions to the trivalent thallium valence state, followed by re-combination of further quantities of said enol ether and said trivalent thallium ion mixture to form additional quantities of said 2-aryl-$C_3$ to $C_6$-alkanoate ester.

2. A process according to claim 1 wherein the trivalent thallium ions needed for further reaction with the enol ether are regenerated one or more times from monovalent thallium ions in the enol ether/ester reaction mixture by admixing with said mixture the perorganic acid and the non-thallium reactive metal in amounts sufficient to oxidize monovalent thallium ions in said mixture to the trivalent thallium valence state in said reaction mixture.

3. A process according to claim 1 wherein the trivalent thallium ions needed for further reaction with the enol ether are regenerated from monovalent thallium ions in a vessel separate from the enol ether/ester product reaction vessel by separating a liquid phase rich in monovalent thallium ions from a liquid phase rich in enol ether or ester product, admixing with the liquid phase containing monovalent thallium ions with the perorganic acid and the non-thallium oxidation promoter metal form in an amount sufficient to oxidize monovalent thallium ions therein to the trivalent thallium valence state, and then returning said liquid phase rich in trivalent thallium ions to the vessel containing enol ether for conversion thereof to the ester product.

4. A process according to claim 1 wherein the trivalent thallium ions are regenerated from monovalent thallium ions in the enol ether reaction mixture by providing the peracid to said enol ether or trivalent thallium ion deficient mixture in the presence of a reactive form of manganese.

5. A process according to claim 4 wherein the manganese is selected from the group consisting of manganese $C_1$ to $C_6$-alkanoate salts, manganese sulfate, manganese chloride or bromide, manganese dioxide, and an alkali metal permanganate.

6. A process according to claim 1 wherein the trivalent thallium ions are regenerated from monovalent thallium ions in the mixture by providing peracetic acid in the presence of a reactive form of ruthenium.

7. A process according to claim 6 wherein the ruthenium is present as ruthenium dioxide.

8. A process according to claim 4 wherein the trivalent thallium ions needed for further reaction are generated by using peracetic acid with manganese to oxidize monovalent thallium ions in the mixture.

9. A process according to claim 1 wherein the thallium salt is thallium acetate, the organic liquid contains aqueous acetic acid, the non-thallium reactive metal compound is a manganese acetate salt, and peracetic acid is used as the perorganic acid to oxidize monovalent thallium ions to trivalent thallium ions.

10. A process in accordance with claim 9 wherein in the reaction between the enol ether (III) and the trivalent thallium ions to form the ester product (I) and the monovalent thallium ions takes place in a two-phase liquid system comprising aqueous acetic acid as one phase and a $C_5$ to $C_{10}$-hydrocarbon as the other liquid phase.

11. A process according to claim 10 wherein the $C_5$ to $C_{10}$-hydrocarbon phase is hexane or a mixture of hydrocarbons containing n-hexane having a boiling point range of about 60° to 68° C. at atmospheric pressure.

12. In a process for preparing $C_1$ to $C_6$-alkyl ester of ibuprofen by reacting a 4-isobutylpropiophenone $C_1$ to $C_6$-alkyl enol ether with trivalent thallium ions in an organic liquid mixture containing an aqueous $C_1$ to $C_{10}$-alkanoic acid, the improvement which comprises regenerating trivalent thallium ions consumed in the enol ether conversion reaction by reacting resulting monovalent thallium ions with a percarboxylic acid have a pKa above 2 in an amount at least stoichiometrically equivalent to the monovalent thallium ion content in the presence of a reactive form of a metal selected from the group consisting of manganese, ruthenium, cobalt, iridium, hafnium, osmium and neobium, said non-thallium reactive metal being provided in a sufficiently soluble form and in an amount sufficient to promote oxidation of monovalent thallium ions to the trivalent thallium valence state, for re-use of the trivalent thallium ions to react with additional enol ether reactant.

13. A process according to claim 12 wherein the thallium ions are provided to the mixture as acetate salts, the non-thallium reactive metal is a manganese acetate, and peracetic acid is used to oxidize monovalent thallium ions to the trivalent thallium valence state in a two-phase solvent system.

14. A process according to claim 13 wherein the two-phase solvent system comprises aqueous acetic acid for the thallium ion phase and a $C_5$ to $C_{10}$-hydrocarbon liquid for the enol ether phase.

* * * * *